(12) United States Patent
Ross et al.

(10) Patent No.: US 6,472,423 B1
(45) Date of Patent: Oct. 29, 2002

(54) PHARMACEUTICAL COMPOSITION

(75) Inventors: Svante Ross, Södertälje (SE); Seth-Olov Thorberg, Strängnäs (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/462,707

(22) PCT Filed: Nov. 23, 1999

(86) PCT No.: PCT/SE99/02176

§ 371 (c)(1),
(2), (4) Date: Jan. 11, 2000

(87) PCT Pub. No.: WO00/32187

PCT Pub. Date: Jun. 8, 2000

(30) Foreign Application Priority Data

Nov. 27, 1998 (SE) .............................. 9804126

(51) Int. Cl.[7] .............................................. A61K 31/35
(52) U.S. Cl. ..................................... 514/456; 514/238.2
(58) Field of Search .............................. 514/238.2, 456

(56) References Cited

U.S. PATENT DOCUMENTS 3,000,903 A * 9/1961 Biel ........................ 260/340.5
5,616,610 A * 4/1997 Evenden et al. ............. 514/456

OTHER PUBLICATIONS

The Journal of Pharmacology and Experimental Therapeutics, vol. 283, No. 1, 1997, Lars Johansson et al., "The Pharmacological Characterization of a Novel Selective 5–Hydroxytryptamine 1A Receptor Antagonist, NAD–299", pp. 216–225.

European Journal of Pharmacology, vol. 320, 1997, Trevor Sharp et al., "Effects of co–administration of a monoamine oxidase inhibitor and a 5–HT1A receptor antagonist on 5–hydroxytrypta–mine cell firing and release", pp. 15–19.

* cited by examiner

*Primary Examiner*—Frederick Krass
(74) *Attorney, Agent, or Firm*—White & Case LLP

(57) ABSTRACT

The invention relates to a composition comprising of a first component (a) which is (R)-3-N,N-dicyclobutylamino-8-fluoro-3,4-dihydro-2H-1-benzopyran-5-carboxamide in the form of the free base, pharmaceutically acceptable salts and/or solvates thereof, and a second component (b) which is a monoamine oxidase (MAO) inhibitor in the form of the free base, pharmaceutically acceptable salts and/or solvates thereof, the preparation thereof, pharmaceutical formulations containing said composition, a kit containing said composition, use of and a method of treatment of affective disorders such as mood disorders and anxiety disorders with said composition.

19 Claims, 1 Drawing Sheet

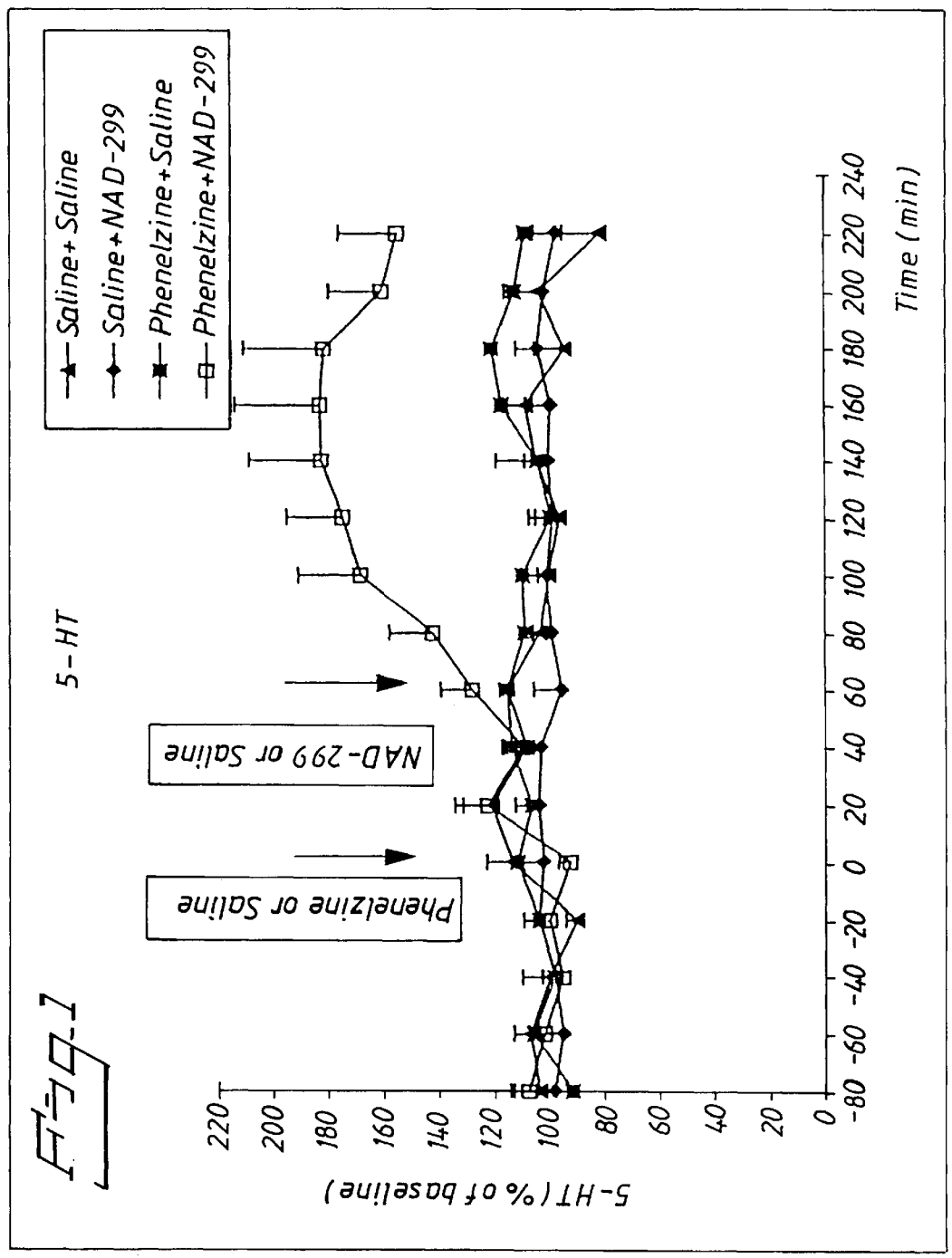

PHARMACEUTICAL COMPOSITION

This application is a 371 of PCT/SE 99/02176, filed Nov. 23, 1999.

FIELD OF THE INVENTION

The present invention relates to a composition which comprises a first component (a) which is (R)-3-N,N-dicyclobutylamino-8-fluoro-3,4-dihydro-2H-1-benzopyran-5-carboxamide in the form of the free base, pharmaceutically acceptable salts and/or solvates thereof, and a second component (b) which is a monoamine oxidase (MAO) inhibitor. The present invention also relates to a process for the preparation of the composition of the invention, pharmaceutical formulations containing said composition and to the use of said composition either by concomitant administration or by separate administration as an improvement of the treatment of affective disorders such as depression, anxiety, obsessive compulsive disorder (OCD), etc.

BACKGROUND OF THE INVENTION

Today, it is generally considered that antidepressants take 2-4 weeks to reach full clinical effect. In contrast, the side effects occur immediately. Thus, slow onset of action of antidepressants leads to a vulnerable period for patients in which they experience the side effects, but not the therapeutic effects of drugs. There is often a heavy burden on the treating physician to persuade the patient to continue with the treatment during this period. Furthermore, in suicidal patients, as the onset of action is gradual, initiative may be regained without the experiencing of full reversal of symptoms, leaving a window of risk for suicide and a frequent requirement for hospitalization. An antidepressant with fast onset of action would not only be beneficial due to the faster symptom reduction, but would also be more acceptable to patients and physicians and reduce the need for and duration of hospitalization. The same long period to reach full clinical effect has been shown in the treatment of other affective disorders such as anxiety and OCD.

PRIOR ART

Effects of co-administration of a 5-HT$_{1A}$ receptor antagonist and a monoamine oxidase inhibitor has been reported in European Journal of Pharmacology 320 (1997), 15–19.

SUMMARY OF THE INVENTION

The present invention is directed to a new composition comprising of a first component (a) to which is (R)-3-N,N-dicyclobutylamino-8-fluoro-3,4-dihydro-2H-1-benzopyran-5-carboxamide in the form of the free base, pharmaceutically acceptable salts and/or solvates thereof, and a second component (b) which is a monoamine oxidase (MAO) inhibitor. Said composition attains a faster onset of action and consequently results in a more efficacious treatment of the patients suffering from affective disorders, particularly depression.

The 5-HT transmission in the brain is negatively regulated by somatodrendritic 5-HT$_{1A}$ receptors (rate of cell firing) and the terminal h5-HT$_{1B}$ receptors (release of 5-HT). MAO inhibitors decrease the transmission of 5-HT by acting at both these sites. An antagonist of the somatodrendritic 5-HT$_{1A}$ receptors prevents the inhibition of the 5-HT release at the nerve terminals resulting in an elevated concentration of synaptic 5-HT showing that antagonists of 5-HT$_{1A}$ receptors may have a clinical potential to improve the efficacy of MAO inhibitors and offer a new rationale for rapid onset of effect in the treatment of affective disorders, for instance the antidepressant actions.

The compound (R)-3-N,N-dicyclobutylamino-8-fluoro-3,4-dihydro-2H-1-benzopyran-5 carboxamide in the form of the free base, pharmaceutically acceptable salts and/or solvate thereof, as a selective 5-HT$_{1A}$ receptor antagonist, is known from WO 95/11891.

The specific salt (R)-3-N,N-dicyclobutylamino-8-fluoro-3,4-dihydro-2H-1-benzopyran-5 carboxamide hydrogen (2R,3R)-tartrate monohydrate disclosed herein is described in the J. Pharmacol. Exp. Ther., 283, 216-225, (1997) as a selective 5-HT$_{1A}$ receptor antagonist. The (R)-3-N.N-dicyclobutylamino-8-fluoro-3,4-dihydro-2H-1-benzopyran-5-carboxamide is in the form of the free base, a pharmaceutically acceptable salt and/or solvate thereof. Both organic and inorganic acids can be employed to form non-toxic pharmaceutically acceptable acid addition salts of the compounds of this invention. Illustrative acids are sulfuric, nitric, phosphoric, oxalic, hydrochloric, formic, hydrobromic, citric, acetic, lactic, tartaric, dibenzoyltartaric, diacetyltartaric, pamoic, ethanedisulfonic, sulfamic, succinic, propionic, glycollic; malic, gluconic, pyruvic, phenylacetic, 4-aminobenzoic, anthranilic, salicylic, 4-aminosalicylic, 4-hydroxybenzoic, 3,4-dihydroxybenzoic, 3,5-dihydroxvbenzoic, 3-hydroxy-2-naphthoic, nicotinic, methanesulfonic, ethanesulfonic, hydroxyethanesulfonic, benzenesulfonic, p-toluenesulfonic, sulfanilic, naphthalenesulfonic, ascorbinic, cyclohexylsulfamic, fumaric, maleic and benzoic acids. These salts are readily prepared by methods known in the art. Illustrative solvates are hydrates such as monohydrate, dihydrate, trihydrate, sesquihydrate or alcoholates such as ethanolate, isopropanolate.

Preferably the active substance is (R)-3-N,N-dicyclobutylamino-8-fluoro-3,4-dihydro-2H1-benzopyran-5-carboxamide hydrogen tartrate. The tartrate comprises the optical forms (2R,3R), (2R,3S) and (2S,3S). Of these forms (R)-3-N,N-dicyclobutylamino-8-fluoro-3,4-dihydro-2H-1-benzopyran-5-carboxamide hydrogen (2R,3R)-tartrate is preferred. The most preferred substance is (R)-3-N,N-dicyclobutylamino-8-fluoro-3,4-dihydro-2H-1-benzopyran-5-carboxamide hydrogen (2R,3R)-tartrate monohydrate.

Suitable known monoamine oxidase inhibitors (MAOI:s) to be used are moclobemide, phenelzine, tranylcypramine and brofaromide, preferably moclobemide or phenelzine.

However, component (b) according to the invention is not limited only to these MAOI:s.

The definition and the chemical names of the above mentioned compounds (MAOI:s) can be found in the Merck Index, 12$^{th}$ Edition, S Budavari et al (ed.) and are incorporated herein by reference.

A preferred composition of the present invention is a composition wherein the first component (a) is (R)-3-N,N-dicyclobutylamino-8-fluoro-3,4-dihydro-2H-1-benzopyran-5-carboxamide hydrogen (2R,3R)-tartrate monohydrate and the second component (b) is pheneizine.

As well as including a monoamine oxidase inhibitor which is commercially available in a racemic form the invention also includes the corresponding optical isomeric forms of the compound having the same structure formula and possessing monoamine oxidase inhibitory activity. If the MAOI is in the form of an optical isomer, other isomers or the racemate of the same structural formula which possess monoamine oxidase inhibitory activity are also included in the invention.

The monoamine oxidase inhibitors may be used in the form of the free base, pharmaceutically acceptable salts and/or solvates thereof and all forms are included in the present invention. What is said above about salts and solvates regarding component (a) is also applicable to component (b).

The composition according to the present invention may exist in one pharmaceutical formulation comprising of (R)-3-N,N-dicyclobutylamino-8-fluoro-3,4-dihydro-2H-1-benzopyran-5-carboxamide in the form of the free base, pharmaceutically acceptable salts and/or solvates thereof, and the monoamine oxidase (MAO) inhibitor, or in two different pharmaceutical formulations, one for (R)-3-N,N-dicyclobutylamino-8-fluoro-3,4-dihydro2-H-1-benzopyran-5-carboxamide in the form of the salts and/or solvates thereof and one for the monoamine oxidase inhibitor. The pharmaceutical formulation may be in the form of tablets or capsules, powders, mixtures, solutions or other suitable pharmaceutical formulation forms such as patches and nasal formulations.

The composition of the present invention can be prepared such that (R)-3-N,N-dicyclobutylamino-8-fluoro-3,4-dihydro-2H-1-benzopyran-5-carboxamid in the form of the free base, pharmaceutically acceptable salts and/or solvates thereof is incorporated into the same pharmaceutical formulation as the monoamine oxidase (MAO) inhibitor by e.g. mixing in a conventional way.

The present invention also includes a method of improving the onset of therapeutic action by concomitant administration of a composition comprising a first component (a) which is (R)-3-N,N-dicyclobutylamino-8-fluoro-3,4-dihydro-2H-1-benzopyran-5-carboxamide in the form of the free base, pharmaceutically acceptable salts and/or solvates and a second component (b) which is a monoamine oxidase inhibitor.

A further embodiment of the present invention is a kit containing a dosage unit of a first component (a) which is (R)-3-N,N-dicyclobutylamino-8-fluoro-3,4-dihydro-2H-1-benzopyran-5-carboxamide in the form of the free base, pharmaceutically acceptable salts and/or solvates, and a dosage unit of a second component (b) which is a monoamine oxidase inhibitor, optionally with instructions for use.

Pharmaceutical Formulations

According to the present invention the compounds in the composition will normally be administered orally, rectally, transdermally, nasally or by injection, in the form of pharmaceutical formulations comprising the active ingredient either as a the free base, a solvate, e.g. hydrates, or a pharmaceutically acceptable non-toxic acid addition salt, e.g. the hydrochloride, hydrobromide, lactate, acetate, phosphate, sulfate, sulfamate, citrate, tartrate, oxalate and the like in a pharmaceutically acceptable dosage form. The dosage form may be a solid, semisolid or liquid formulation. Usually the active substances will constitute between 0.1 and 99% by weight of the formulation, more specifically between 0.5 and 20% by weight for formulations intended for injection and between 0.2 and 50% by weight for formulations suitable for oral administration.

The pharmaceutical formulation comprises the active ingredients, optionally in association with adjuvants, diluents, excipients and/or inert carriers.

To produce pharmaceutical formulations of the composition of the invention in the form of dosage units for oral application, the selected compounds may be mixed with a solid excipient, e.g. lactose, saccharose, sorbitol, mannitol, starches such as potato starch, corn starch or amylopectin, cellulose derivatives, a binder such as gelatin or polyvinylpyrrolidone, disintegrants e.g. sodium starch glycolate, cross-linked PVP and cross-caramnellose sodium; a lubricant such as magnesium stearate, calcium stearate, polyethylene glycol, waxes, paraffin, and the like, and an antisticking agent such as talc or colloidal silicon dioxide, and then compressed into tablets. If coated tablets are required, the cores, prepared as described above, may be coated with a polymer known to the man skilled in the art, e.g. HPMC, HC or other cellulose derivatives or PVP, wherein the polymer is dissolved in water or a readily volatile organic solvent or mixture of organic solvents. Alternatively, the tablets can be coated with a concentrated sugar solution which may contain e.g. gum arabic, gelatine, talcum, titanium dioxide, and the like. Dyestuffs may be added to these coatings for instance in order to readily distinguish between tablets containing different active substances or different amounts of the active compounds.

For the formulation of soft gelatin capsules, the active substances may be admixed with e.g. a vegetable oil or polyethylene glycol. Hard gelatin capsules may contain granules of the active substances using any of the above mentioned excipients for tablets, e.g. lactose, saccharose, sorbitol, mannitol, starches (e.g. potato starch, corn starch or amylopectin), cellulose derivatives, plasticizer, polyethene glycol, waxes, lipids or gelatin. Also liquids or semisolids of the drug can be filled into hard gelatin capsules.

Dosage units for rectal application can be solutions or suspensions or can be prepared in the form of suppositories comprising the active substances in a mixture with a neutral fatty base, or gelatin rectal capsules comprising the active substances in admixture with vegetable oil or paraffin oil. Liquid formulations for oral application may be in the form of solutions, syrups or suspensions, for example solutions containing from about 0.2% to about 20% by weight of the active substances herein described, the balance being sugar and mixture of ethanol, water, glycerol and propylene glycol. Optionally such liquid formulations may contain colouring agents, flavouring agents, saccharin and carboxymethylcellulose as a thickening agent or other excipients known to a person skilled in the art.

Solutions for parenteral applications by injection can be prepared in an aqueous solution of a water-soluble pharmaceutically acceptable salt of the active substances, preferably in a concentration of from about 0.5% to about 10% by weight. These solutions may also contain stabilizing agents and/or buffering agents and may conveniently be provided in various dosage unit ampoules.

Suitable daily doses of the active compounds in the composition of the invention in therapeutic treatment of humans are about 0.01–100 mg/kg bodyweight for peroral administration and 0.001–100 mg/kg bodyweight for parenteral administration. The daily doses of the active ingredient component (a) may very well differ from the daily doses of the active ingredient component (b) in the form of the free base, pharmaceutically acceptable salts and/or solvate thereof but the doses can also be the same for both of the active ingredients.

Medical and Pharmaceutical Use

In a further aspect the present invention provides the use of the composition comprising a first component (a) which is (R)-3-N,N-dicyclobutylamino-8-fluoro-3,4-dihydro-2H-1benzopyran-5-carboxamide in the form of the free base, pharmacuetically acceptable salts and/or solvates and a second component (b) which is a monoamine oxidase inhibitor, in the treatment of 5-hydroxytryptamine mediated disorders, such as affective disorders. Examples of affective disorders are disorders in the CNS such as mood disorders (depression, major depressive episodes, dysthymia, seasonal affective disorder, depressive phases of bipolar disorder), anxiety disorders (obsessive compulsive disorder, panic disorder with/without agoraphobia, social phobia, specific phobia, generalized anxiety disorder, posttraumatic stress disorder), personality disorders (disorders of impulse control, trichotellomania) and sleep disorders. Other disorders in the CNS such as eating disorders (obesity, anorexia, bulimia), premenstrual syndrome, sexual disturbances, alcoholism, tobacco abuse, autism, attention deficit, hyperactivity disorder, migraine, memory disorders (age associated memory impairment, presenile and senile dementia such as Alzheimer's disease), pathological aggression, schizophrenia, endocrine disorders (e g hyperprolactinaemia), stroke, dyskinesia, Parkinson's disease, thermoregulatory disorders, pain and hypertension may also be treated with the combination described herein. Examples of other hydroxytryptamine mediated disorders are urinary incontinence, vasospasm and growth control of tumors (e g lung carcinoma) and it may be possible to treat those with the combination described herein as well.

Pharmacology

Method for Testing

The effect of a 5-$HT_{1A}$ receptor antagonist in combination with a monoamine oxidase inhibitor on extracellular levels of 5-HT in the frontal cortex of rats as measured by in vivo microdialysis.

Male sprague-Dawley rats (B&K, International AB, Sollentuna, Sweden) weighing 270-320 g, were anaesthetized by inhalation of Enfluran (Efrane®) and placed in a stereotaxic frame. An unilateral guide cannula was carefully implanted into the frontal cortex using the following stereotaxic coordinates with respect to bregma: AP:−3.5 mm, L:−3.0 mm and DV: 0 mm from the brain surface. The animals were then allowed to recover for 2–7 days before the experiments were carried out. The day before starting dialysis sampling, microdialysis probes with 3 mm membranes were inserted into the guide cannula with Ringer solution at a flow rate of 0.1 $\mu$l/min. On the day of the experiment, the probes were perfused with Ringer solution at a flow rate of 2.0 $\mu$l/min. and samples were collected every 20 min. Compound B (10 mg/kg, monoamine oxidase inhibitor, MAOI) or saline was given at time 0 min and Compound A (1.0 mg/kg, 5-$HT_{1A}$ antagonist) or saline was administered 60 min later. All drugs were given subcutaneously. The 5-HT content was analyzed by high performance liquid chromatography (HPLC) with electrochemical detection. For data analysis, the average 5-HT value of 4 samples collected preadministration of drugs was defined as 100% (baseline) and the following samples expressed as percentage of this value.

BRIEF DESCRIPTION OF THE DRAWINGS

FIG. 1 shows the effects of Compound B in combination with Compound A on extracellular levels of 5-HT in the rat frontal cortex. The values are expressed as percentages of baseline; means+S.E.M (n=4–6 per group). The arrows indicate drug administration.

Compound A: (R)-3-N,N-dicyclobutylamino-8-fluoro-3, 4-dihydro-2H-1-benzopyran-5-carboxamide hydrogen (2R, 3R) tartrate monohydrate, AND-2991.

Compound B: Phenelzine

What is claimed is:

1. A composition comprising a first component (a) which is (R)-3-N,N-dicyclobutylamino-8-fluoro-3,4-dihydro-2H-1-benzopyran-5-carboxamide in the form of the free base, or a pharmaceutically acceptable salt or solvate thereof, and a second component (b) which is a monoamine oxidase inhibitor in the form of the free base, or a pharmaceutically acceptable salt or solvate thereof.

2. The composition according to claim 1 wherein the first component (a) is (R)-3-N,N-dicyclobutylarnino-8-fluoro-3, 4-dihydro-2H-1-benzopyran-5-carboxamide hydrogen tartrate.

3. The composition according to claim 2 wherein the first component (a) is (R)-3-N,N-dicyclobutylamino-8-fluoro-3, 4-dihydro-2H-1-benzopyran-5-carboxamide hydrogen (2R, 3R)-tartrate.

4. The composition according to claim 3 wherein the first component (a) is (R)-3-N,N-dicyclobutylamino-8-fluoro-3, 4-dihydro-2H-1-benzopyran-5-carboxamide hydrogen (2R, 3R)-tartrate monohydrate.

5. The composition according to claim 1, wherein the monoamine oxidase inhibitor is moclobemide or pbenelzine.

6. The composition according to claim 1 wherein the first component (a) is (R)-3-N,N-dicyclobutylamino-8-fluoro-3, 4-dihydro-2H-1-benzopyran-5-carboxamide hydrogen (2R, 3R)-tartrate monohydrate and the second component (b) is phenelizine.

7. The composition according to claim 2 wherein the monoamine oxidase inhibitor is moclobemide or phenelzine.

8. The composition according to claim 3 wherein the monoamine oxidase inhibitor is moclobemide or phenelzine.

9. The composition according to claim 4 wherein the monoamine oxidase inhibitor is moclobemide or phenelzine.

10. A kit containing a dosage unit of a first component (a) which is (R)-3-N,N-dicyclobutylamino-8-fluoro-3,4-dihydro-2H-1-benzopyran-5-carboxamide in the form of the free base, or a pharmaceutically acceptable salt or solvate thereof; and (b) a dosage unit of a second unit of a second component which is a monoamine oxidase inhibitor in the form of a free base, or a pharmaceutically acceptable salt or solvate thereof, optionally with instructions for use.

11. The kit of claim 10, wherein the first component (a) is selected from the group consisting of:

(R)-3-N,N-dicyclobutylamino-8-fluoro-3,4-dihydro-2H-1-benzopyran-5-carboxamide hydrogen tartrate;

(R)-3-N,N-dicyclobutylamino-8-fluoro-3,4-dihydro-2H-1-benzopyran-5-carboxamide hydrogen (2R,3R)-tartrate; and, (R)-3-N,N-dicyclobutylamino-8-fluoro-3,4-dihydro-2H-1-benzopyran-5-carboxamide hydrogen (2R,3R)-tartrate monohydrate; and the second component (b) is selected from the group consisting of moclobemide and phenelzine.

12. A method for the treatment of 5-HT mediated disorders by administering to a patient suffering therefrom the composition defined in any one of claims 1–6 or 7–9.

13. The method according to claim 12 for the treatment of affective disorders.

14. The method according to claim 12 for the treatment of mood disorders.

15. The method according to claim 14 for the treatment of depression.

16. A method of improving the onset of therapeutic action of component (b) by concomitant administration of a composition comprising component (a), as defined in any one of claims 1–6 or 7–9.

17. A pharmaceutical formulation wherein the active ingredients are those of the composition defined in any one of claims 1–6 or 7–9, optionally in association with adjuvants, excipients, or inert carriers.

18. A process for the preparation of the composition according to any one of claims 1–6 or 7–9, wherein component (a) is incorporated into the same pharmaceutical formulation as component (b).

19. A process for the preparation of the composition according to any one of claims 1–6 or 7–9, wherein component (a) is in one pharmaceutical formulation and is combined with component (b) in a different pharmaceutical formulation.

* * * * *